(12) United States Patent
McNally et al.

(10) Patent No.: US 7,828,792 B2
(45) Date of Patent: Nov. 9, 2010

(54) MRI COMPATIBLE PROGRAMMABLE VALVE PUMP

(75) Inventors: Jason McNally, Brighton, MA (US); David Morrison, Pawtucket, RI (US); Constantin Matchey, West Kingston, RI (US)

(73) Assignee: Medasys Incorporated, Mount Olive, NJ (US)

( * ) Notice: Subject to any disclaimer, the term of this patent is extended or adjusted under 35 U.S.C. 154(b) by 194 days.

(21) Appl. No.: 12/220,593

(22) Filed: Jul. 25, 2008

(65) Prior Publication Data

US 2010/0021311 A1    Jan. 28, 2010

(51) Int. Cl.
*A61K 9/22* (2006.01)
(52) U.S. Cl. .................................. 604/891.1
(58) Field of Classification Search .............. 604/891.1, 604/892.1, 67, 131
See application file for complete search history.

(56) References Cited

U.S. PATENT DOCUMENTS

| | | | |
|---|---|---|---|
| 4,646,781 A * | 3/1987 | McIntyre et al. ......... 137/512.4 |
| 4,838,887 A | 6/1989 | Idriss ....................... 604/891.1 |
| 5,049,141 A | 9/1991 | Olive ....................... 604/891.1 |
| 5,207,666 A * | 5/1993 | Idriss et al. .............. 604/891.1 |
| 5,220,943 A * | 6/1993 | Zink ...................... 137/565.17 |
| 2005/0098413 A1 | 5/2005 | Uehira ....................... 200/5 R |
| 2005/0189508 A1 | 9/2005 | Beswick et al. |

OTHER PUBLICATIONS

International Search Report and Written Opinion dated Sep. 1, 2009.

* cited by examiner

*Primary Examiner*—Melba Bumgarner
(74) *Attorney, Agent, or Firm*—Armstrong Teasdale LLP

(57) ABSTRACT

An implantable drug delivery system utilizing a non-magnetic valve/accumulator metering assembly is disclosed. The solenoids of the prior art, which respond to magnetic fields, are replaced by Shape Memory Alloy (SMA) wires and associated control electronics. By exploiting the inherent characteristics of SMA wires, which can expand and contract based on their temperature, the movements required to actuate the metering assembly can be achieved. This configuration retains the benefits associated with the prior art, while eliminating the major drawback.

9 Claims, 6 Drawing Sheets

MRI COMPATIBLE PROGRAMMABLE VALVE PUMP

BACKGROUND OF THE INVENTION

Implantable valve accumulator pump systems for the delivery of mediation or other fluids to a patient are well known and described in U.S. Pat. Nos. 4,838,887 and 5,049,141, the disclosures of which are hereby incorporated by reference.

U.S. Pat. Nos. '887 and '141 disclose an implantable valve accumulator pump system for the delivery of infusate, such as medication. The implantable pump portion is comprised of four essential assemblies, as shown in FIG. 1. The first major assembly is a rechargeable, constant pressure drug reservoir 10 in series with a bacteria/air filter 24. In one embodiment, the reservoir 10 comprises a sealed housing 14 containing a bellows 16. The bellows 16 separates the housing 14 into two parts. Chamber 18 is used to hold the drug or other medicinal fluid. Second zone 20 is normally filled with a two-phase fluid, such as Freon®, that has a significant vapor pressure at body temperature. Thus, as the fluid within the second zone 20 vaporizes, it compresses the bellows 16, thereby pressurizing the drug in the chamber 18. The drug can be refilled via septum 12.

The two-phase fluid helps maintain the chamber 18 under a constant pressure. When the chamber is refilled, the two-phase fluid is pressurized thereby condensing a portion of the vapor and converting it to liquid. As the chamber 18 is emptied, this liquid vaporizes, thus maintaining the pressure on the bellows 16.

Since the infusate in chamber 18 is under positive pressure, it is urged out of the chamber, through a bacterial filter 24 and toward the metering assembly.

The second major assembly is an electronically controlled metering assembly comprising two normally closed solenoid valves 26, 28, which are positioned on the inlet and outlet sides of a fixed volume accumulator 30. The valves are controlled electronically via a module 32, which can be programmed utilizing an external programmer 34. The metering assembly is designed such that the inlet valve 26 and the outlet valve 28 are never simultaneously open.

The third major assembly is an outlet catheter 36 for medication infusion in a localized area. The delivery of fluid occurs at an infusion site that is below the accumulator pressure, thereby forcing discharge through the catheter 36.

The fourth assembly of this system is the external programmer 34 used to communicate and program the desired medication regimen. This programmer is preferably a handheld unit with a touch screen. It provides a data transfer link to the implanted electronics 32 and is able to exchange information with the electronics 32, including but not limited to battery status, diagnostic information, calibration information, etc.

Returning to the metering assembly, FIG. 2 illustrates the normal sequence used to fill and dispense infusate. The valves in the medication metering assembly alternately open and close to admit infusate from the reservoir 18 into the accumulator 30, via conduit 22, and to dispense a precise volume spike to an outlet catheter 36. During the first step, both valves are closed and the accumulator is empty. In this step, no fluid is moved. During the second step, the inlet valve 26 opens while the outlet valve 28 remains closed. Since the incoming fluid is at a higher pressure than the accumulator 30, fluid fills the accumulator. The accumulator preferably has a fixed volume such that exact amounts of fluid can be dispensed. Once the accumulator 30 is filled, no fluid movement occurs. During the third step, the inlet valve 26 closes, thereby separating the reservoir from the accumulator. At this step, the accumulator 30 is filled. Finally, during the fourth step, the outlet valve 28 opens. Since the accumulator 30 is at a higher pressure than the outlet canella, the fluid exits the accumulator through outlet valve 28.

FIG. 3 illustrates the components used in the metering assembly of the prior art. Valves 26 and 28 are implemented as miniature solenoid valves. The valves are preferably disposed in a side-by-side arrangement having two solenoid assemblies 74, each receiving power via a corresponding electrical lead 76. The valves are operably powered to drive a working plunger 78 biased by means of spring 80. The working plunger and return spring assembly are isolated from the solenoids 74 by means of an isolation diaphragm 82. As is customary, the solenoid is actuated by a magnetic field that drives the working plunger 78. Once charged, the solenoid overcomes the force of the bias spring 80, and pulls the plunger 78 off the valve seat 84, allowing fluid flow.

The flow path of the infusate or medicinal fluid is illustrated by the arrows in FIG. 3. As described above, with valve 26 in the open position, fluid communication is established between the accumulator 30 and the inlet conduit 54. The infusate is thereby delivered upward through the valve seat 84 (shown closed in FIG. 3), into the accumulator flow passage 86. The area between the valve seats comprises the accumulator storage space. When valve 26 is closed, the accumulator 30 is isolated from the reservoir 18.

When valve 28 is opened, fluid communication is established between the accumulator and the outlet conduit 55. The infusate is thereby delivered downward from the accumulator storage space, through the valve seat 84 (shown closed in FIG. 3), and into the outlet conduit 55. Furthermore, the system is preferably designed such that valves 26 and 28 cannot be opened at the same time in order to prevent the metering function of the accumulator 30 from being bypassed.

This system is highly effective in most situations. However, when a patient with such a device enters an MRI (magnetic resonant imaging) environment, the presence of large magnetic fields above a certain threshold may affect the operation of the pump's valves such that the metering function of the accumulator is bypassed. Consequently, patients implanted with these devices must be instructed to have the pump reservoir 18 emptied before undergoing an MRI procedure. This prohibition and warning is commonplace for patients implanted with such medical devices.

It would be beneficial for such an implantable drug delivery system to remain operational even in the presence of strong magnetic fields, such as those encountered during MRI procedures.

SUMMARY OF THE INVENTION

The problems of the prior art have been overcome by the present invention through the use of a non-magnetic valve/accumulator metering assembly. The solenoids of the prior art, which are susceptible to magnetic fields, are replaced by Shape Memory Alloy (SMA) wires and associated control electronics. By exploiting the inherent characteristics of SMA wires, which can expand and contract based on their temperature, the movements required to actuate the metering assembly can be achieved. This configuration retains the benefits associated with the prior art, while eliminating the major drawback.

DETAILED DESCRIPTION OF THE INVENTION

As described above, solenoids are used to cause the movement required to open and close the valve assemblies. However, in a magnetized environment, such as an MRI chamber, these solenoids cannot be controlled. Thus, it is possible to bypass the accumulator. To overcome this limitation, the movement, formerly provided by the solenoid, is now provided via a shape metal alloy (SMA) wire.

Shape memory alloys are metals that display property changes as their temperature changes. Most useful is the fact that, at elevated temperatures, these alloys transform to a memorized shape.

Several metals exhibit these properties, including a nickel-titanium alloy, comprising roughly equal parts of each. Other alloys, such as CuAlNi, can also be used. The nickel-titanium alloy is particularly useful because of its electrical characteristics. In wire form, this alloy can be heated simply by passing an electrical current through it. Thus, no external or addition heat generators are required.

As stated above, the SMA wire is actuated preferably by passing current through it, so as to heat the wire. Since an electrical current is passing through the wire, it is preferable to separate the wire from the fluid path in the assembly. A number of different techniques can be utilized to achieve this result.

Figure 1:
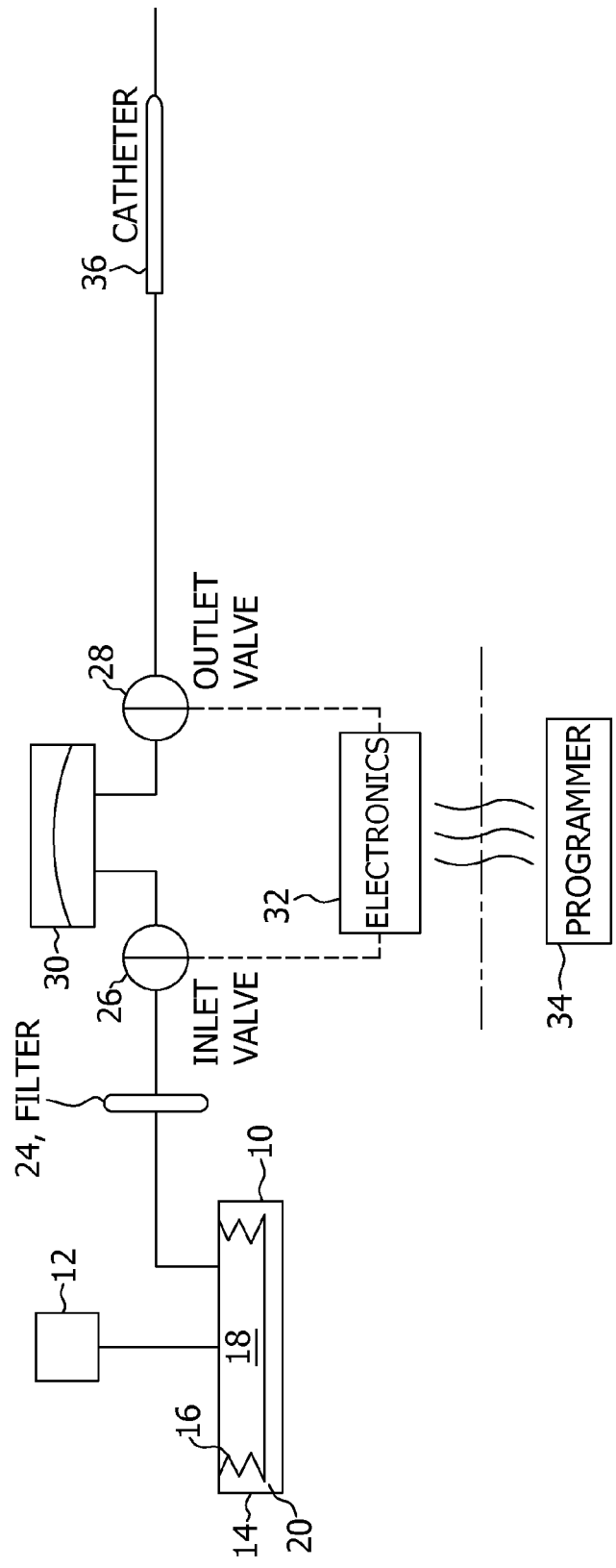
FIG. 1 is a schematic diagram of the implantable drug delivery system of the prior art.
Figure 2:
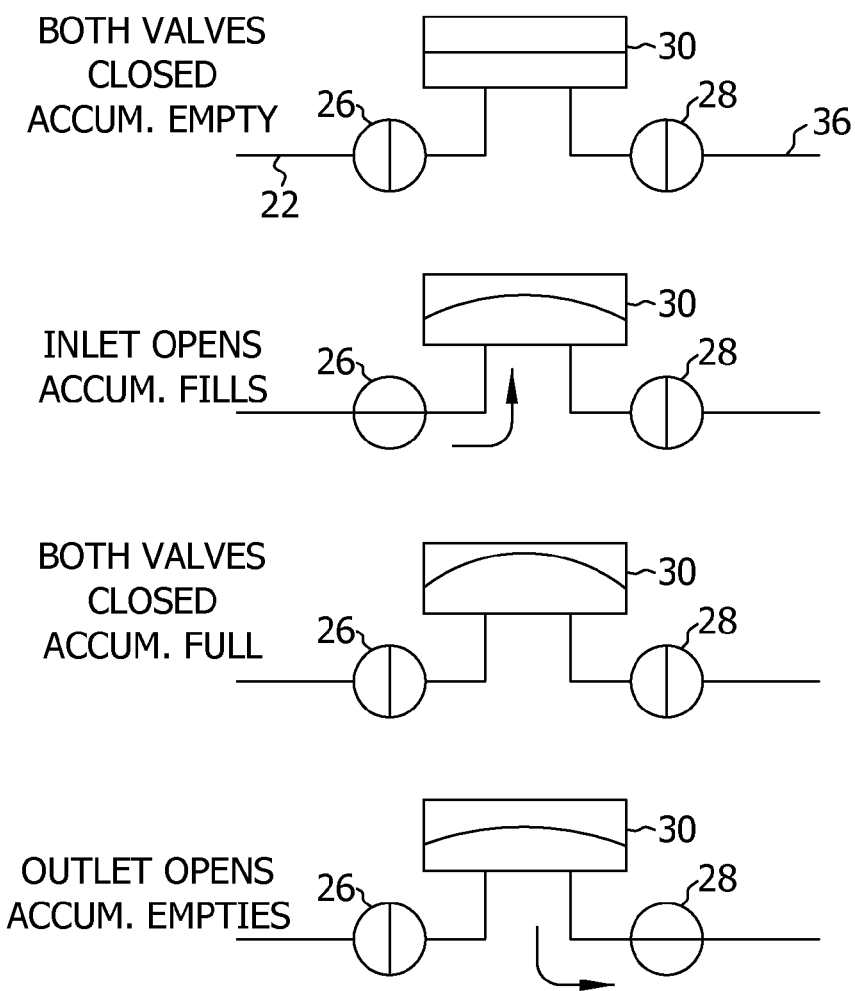
FIG. 2 is a representation of the sequence of steps performed by the metering assembly.
Figure 3:
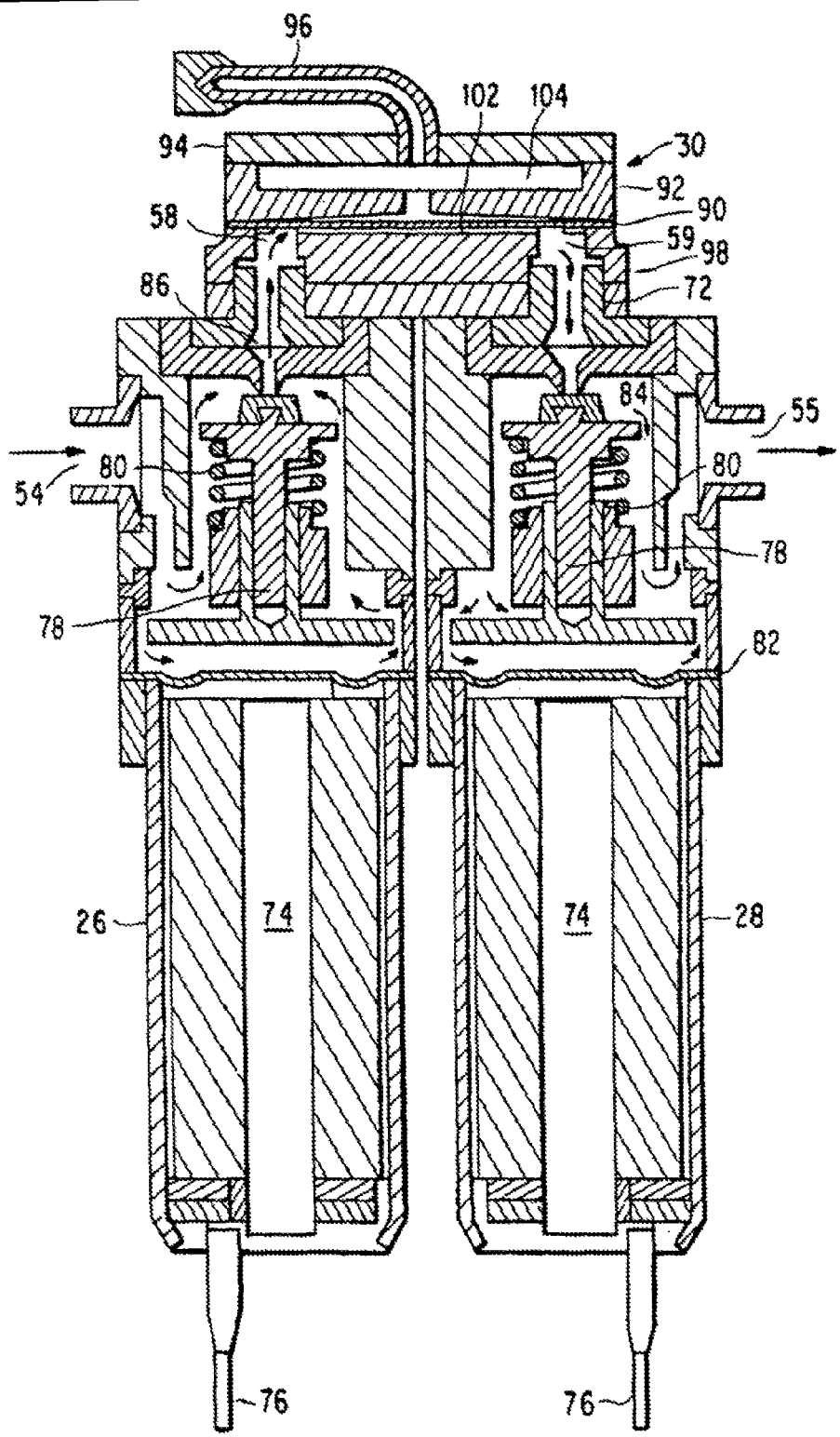
FIG. 3 is a schematic representation of the metering assembly of the prior art.
Figure 4:
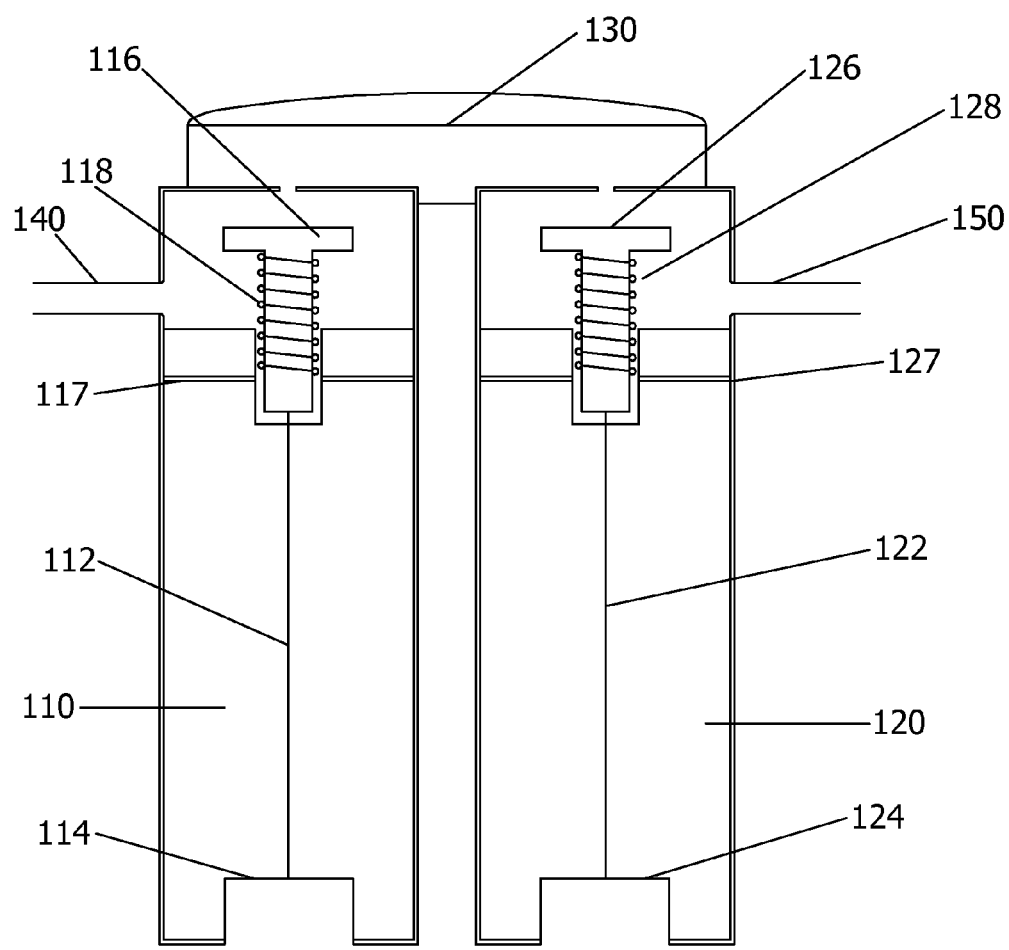
FIG. 4 is a first embodiment of the present invention.

In a first embodiment, shown in FIG. 4, each solenoid is replaced with a single SMA wire. The valve system consists of two valves 110, 120, both in communication with an accumulator 130. The normal or default state of both valves is closed, and each is independently actuated using a respective SMA wire 112, 122. As done in the prior art, the inlet valve 116 is actuated to allow the passage of fluid through the inlet 140 and into the accumulator 130. The accumulator is preferably pressurized with a fluid, such as Argon (Ar) gas. Once the accumulator 130 reaches a maximum volume, such as about 2 μL, the inlet valve 116 can be closed. After the inlet valve 116 has been closed for a period of time, the outlet valve 126 can be safely actuated to allow the accumulator 130 to drain through the outlet valve 126 and through the outlet 150. The device follows the sequence of steps described in FIG. 2.

Each valve is actuated using a respective SMA wire 112, 122. These wires are preferably located outside of the fluid path, since electrical current is passed through them. Thus, the valve is separated into at least two chambers, a fluid chamber through which infusate can flow, and a second chamber in which the SMA wire is attached. Within the fluid chamber is an actuated member, having two settings; a first setting wherein fluid communication occurs between the fluid chamber and the accumulator and a second setting wherein the fluid chamber is isolated from the accumulator.

In one embodiment, one end of a wire is attached to a fixed point 114, 124, while the opposite end is connected to the actuated member, such as plunger assembly 116, 126. The plunger assemblies 116, 126 are preferably attached to flexible fluid impermeable barriers 117, 127 that separate the fluid chamber from the wire chamber of the valve. These flexible fluid impermeable barriers, which can be made of titanium or any other suitable material, deflect as the SMA wire contracts allowing the valve to open. In some embodiments, the SMA wire contracts about 3% of its total length when an electrical current is ran through the wire. This reduction in length pulls the actuated member, such as plunger 116,126 to its first setting, away from the valve seat, thereby allowing the valve to open.

The SMA wire is connected to a power supply through a lead near the fixed point 114, 124. The return path for the current is provided via an insulted lead located near the plunger (not shown). When power is removed from the wire 112, 122, the wire relaxes back to its longer length. A biasing element, such as return spring 118, 128 preferably located inside the fluid path, aids in returning the actuated member, such as plunger 116, 126, to its second setting where it presses against the valve seat. In some embodiments, the plunger is titanium with a molded silicone seat. In addition, in some embodiments, the forces resulting from the deflection of flexible fluid barrier 117, 127 also help return the assembly to the second setting, which is its default position.

As stated above, FIG. 4 depicts an assembly utilizing a fluid barrier to separate the fluid chamber from the wire chamber. This design represents one example of a possible configuration utilizing a flexible fluid barrier. Furthermore, FIG. 4 depicts the use of a plunger assembly as the actuated member used to enable and disable fluid communication between the fluid chamber and the accumulator. Those skilled in the art will appreciate that other designs are also possible and within the scope of the invention.

Figure 5:
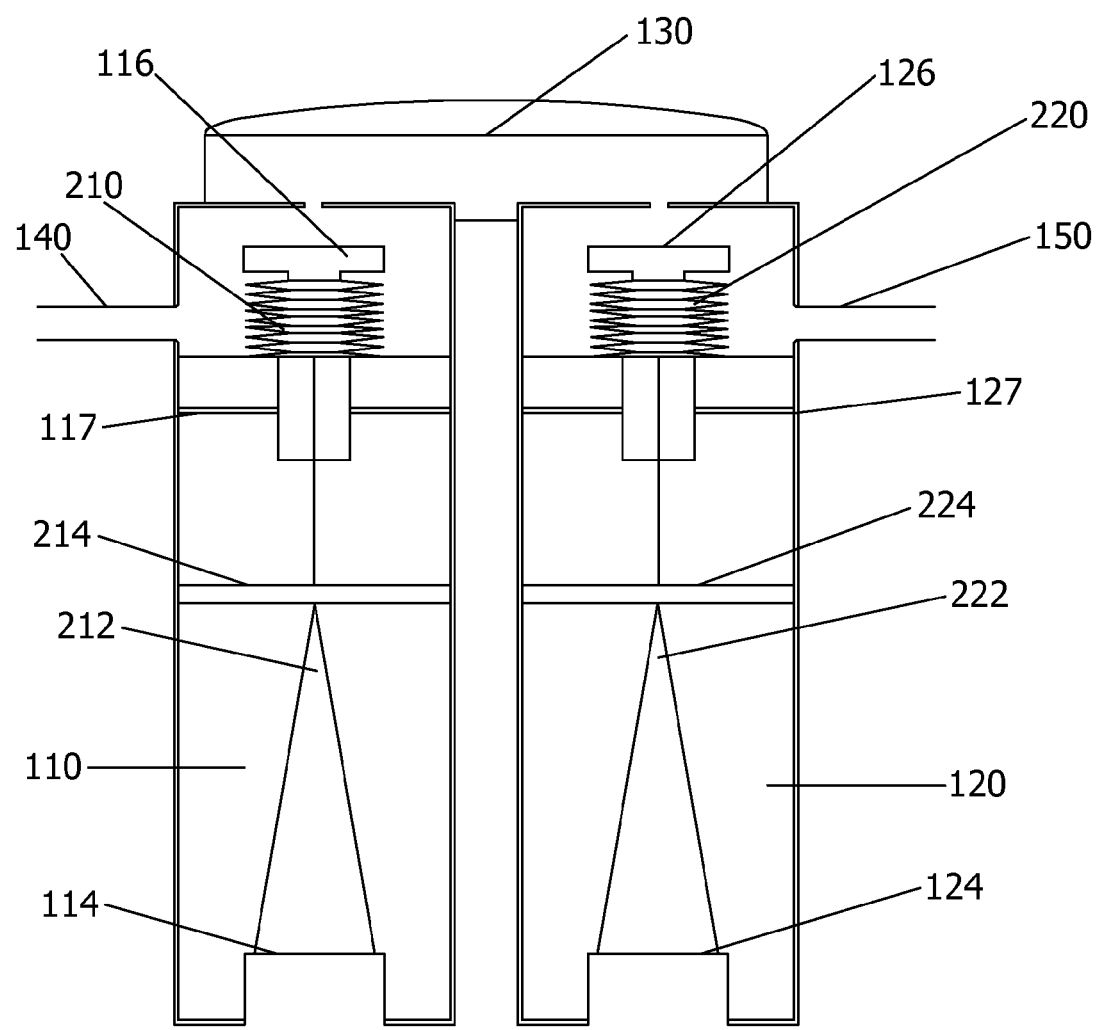
FIG. 5 is a second embodiment or the present invention.

For example, FIG. 5 depicts an assembly utilizing a bellows configuration as another approach to separate the fluid chamber from the wire chamber. The bellows also serves as the actuated member. The bellows is preferably made of titanium with plungers 116, 126 welded to the bellows. The bellows can withstand repeated cycling without any material changes in performance. In this configuration, all similar components are numbered using like reference designators and operate as described above. In this figure, the bellows 210, 220 act as a flexible fluid barrier and replace the springs 118,128 shown in FIG. 4. The bellows 210, 220 is maintained in a slight compressed state when the valve is closed, so as to keep the valve seat engaged. When the SMA wire 212, 222 is energized, it begins to contract. This force further compresses the bellows 210, 220 and causes the valve to open, thereby allowing fluid flow. When power to the wire is removed, the SMA wire relaxes to its original length. In this relaxed state, the spring force from bellows 210, 220 returns the seat to its normally closed position.

This figure shows the SMA wire 212, 222 in a looped configuration. This configuration allows twice the pull forces in a similarly sized physical space. In this configuration, two leads are provided to each valve, one attached to each end of the SMA wire. Either the straight or looped wire design may be used in any of the embodiments. For example, the looped configuration shown in FIG. 5 can be applied to the assembly shown in FIG. 4. Similarly, the straight wire configuration of FIG. 4 can be used in the bellows configuration of FIG. 5.

Figure 6:
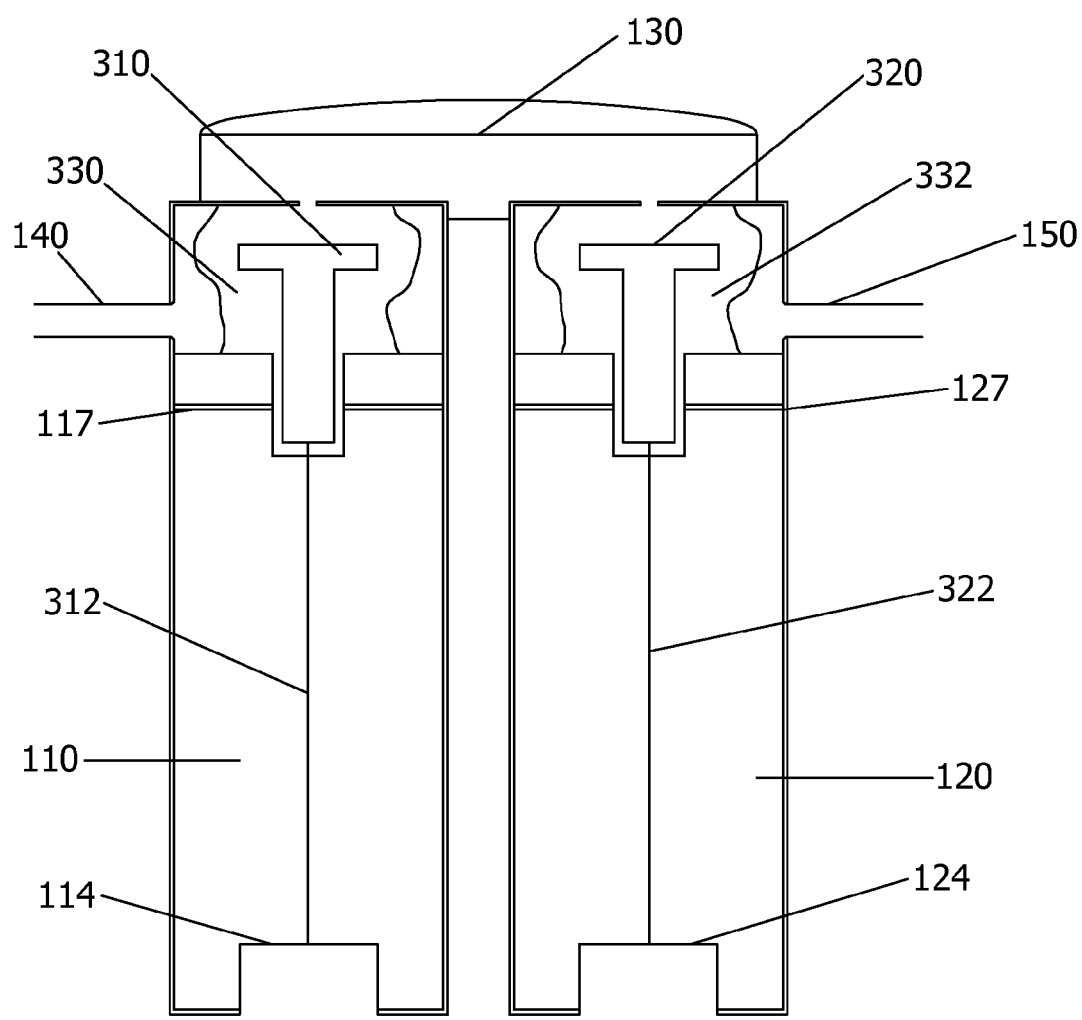
FIG. 6 is a third embodiment of the present invention.

FIG. 6 shows a third embodiment of the assembly of the present invention. In this embodiment, the actuated member is a plunger 310, 320, and is surrounded by an elastic material 330, 332, such as an elastomer. Silicone or a soft plastic material, such as urethane can also be used. The plunger and the surrounding material is sized and shaped such that under normal conditions, the elastic material is under slight compression so as to force the valve seat closed. The plunger and elastic material also serve as a flexible fluid barrier. A SMA wire 312,322, in either a straight or looped configuration, is attached to the bottom of the plunger 310, 320.

When the SMA wire 312, 322 is energized and contracts, the plunger is pulled away from the valve seat. This causes the elastic material to deflect and allows the valve seat to open, thereby allowing fluid flow. When the current through the SMA wire 312, 322 is removed, the wire relaxes to its original length. The spring force from the deflected, or compressed, elastic material pushes toward the valve, and urges the valve seat to its closed position.

In one embodiment, the plunger assembly is a over molded unit where the titanium plungers 310, 320 are over molded with a polymer to form a single unit. In an alternative embodiment, the plunger 310 and the surrounding elastic material 330 are molded as a single unit.

The valve electronic system can be controlled using a closed or open loop system. In an open loop system, a known amount of electrical current is passed through the valve (i.e. the SMA wire) in order to actuate the device. In a closed loop system, there is electrical/mechanical feedback that allows the valve to be opened to the same distance and only applies the amount of current required to actuate the wire to this distance. This feedback can be created in a variety of ways, including but not limited to electronic sensors, or mechanical proximity switches. A closed loop system prevents the wire from over stress and helps to maintain the power at a lower level than in an open loop system, since the current passed through the wire is more tightly regulated. The closed loop system should therefore provide lower power consumption and long cycle life of the SMA wire. However, in certain implementations, the simplicity of an open loop system may be preferable.

Each of these embodiments illustrates the basic requirements associated with the present invention. Because of the current flowing through the SMA wires, the fluid path must be isolated from the wire. While three embodiments are described above, the invention is not so limited. Any mechanism that successfully isolates the fluid chamber from the SMA wire chamber can be used. A second requirement is that there be a biasing element to help stretch the SMA wire back from its energized length to its relaxed length. Again, the present disclosure describes springs, bellows and elastic materials as three embodiments of implementing this biasing element. However, other biasing elements are known in the art and within the scope of the present invention. Finally, an actuated member is required to open and close fluid communications between the accumulator and the fluid chamber

What is claimed is:
1. An implantable infusion apparatus comprising:
   a. a rechargeable positive pressure infusate reservoir;
   b. an electronically controlled metering assembly receiving infusate from said reservoir, said metering assembly comprising a pair of normally closed valves and an accumulator positioned in fluid communication with each of said valves, wherein each of said valves comprises:
      i. a SMA wire, having two lengths; a first longer length in its relaxed state, and a second shorter length in its energized state;
      ii. a fluid chamber in communication with said accumulator having an actuated member having a first setting whereby fluid flow between said fluid chamber and said accumulator is allowed and a second setting whereby said fluid chamber and said accumulator are isolated, a biasing element to urge said SMA wire from its energized length to its relaxed length, such that said actuated member moves to first setting when said wire is energized and moves to said second setting when said wire is relaxed; and
      iii. a fluid tight barrier between said fluid chamber and said SMA wire;
   c. electronic means for controlling the operation of said valves, and
   d. an outlet in fluid communication with said metering assembly to dispense infusate to a site in a living body, when a first of said valves is open, infusate flows from said reservoir into said accumulator and when the second valve is open and said first valve is closed, infusate flows from said accumulator into said outlet, said accumulator storing and discharging predetermined volume spikes of infusate at a frequency determined by the cycling rate of said pair of valves.

2. The implantable infusion apparatus of claim 1, wherein said fluid tight barrier comprises a bellows.

3. The implantable infusion apparatus of claim 1, wherein said actuated member comprises a bellows.

4. The implantable infusion apparatus of claim 1, wherein said biasing element comprises a bellows.

5. The Implantable infusion apparatus of claim 1, wherein said biasing element comprises a spring.

6. The implantable infusion apparatus of claim 1, wherein said actuated member comprises a plunger.

7. The implantable infusion apparatus of claim 1, wherein said biasing element comprises a compressed elastic material.

8. The implantable infusion apparatus of claim 1, wherein said fluid tight barrier comprises a compressed elastic material.

9. The implantable infusion apparatus of claim 1, wherein said electronic means supplies current to said SMA wire to cause said actuated member to move to said first setting.

* * * * *